(12) United States Patent
Nishina et al.

(10) Patent No.: US 12,265,117 B2
(45) Date of Patent: Apr. 1, 2025

(54) PROBE APPARATUS AND MANUFACTURING METHOD FOR PROBE APPARATUS

(71) Applicant: NIHON KOHDEN CORPORATION, Tokyo (JP)

(72) Inventors: Shohei Nishina, Tokorozawa (JP); Mitsuo Oshima, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 17/808,135

(22) Filed: Jun. 22, 2022

(65) Prior Publication Data

US 2023/0003787 A1 Jan. 5, 2023

(30) Foreign Application Priority Data

Jun. 30, 2021 (JP) .................. 2021-108594

(51) Int. Cl.
*G01R 31/28* (2006.01)

(52) U.S. Cl.
CPC ................. *G01R 31/2808* (2013.01)

(58) Field of Classification Search
None
See application file for complete search history.

(56) References Cited

U.S. PATENT DOCUMENTS

| 5,237,994 | A | * | 8/1993 | Goldberger | ........ | A61B 5/14552 |
| | | | | | | 600/323 |
| 6,420,889 | B1 | * | 7/2002 | Terada | ............... | G01R 1/07342 |
| | | | | | | 324/754.07 |

| 2002/0095074 | A1 | 7/2002 | Al-Ali |
| 2011/0306867 | A1 | 12/2011 | Gopinathan et al. |
| 2012/0071782 | A1 | 3/2012 | Patil et al. |
| 2012/0101355 | A1 | 4/2012 | Gopinathan et al. |
| 2012/0101369 | A1 | 4/2012 | Patil et al. |
| 2013/0123694 | A1 | 5/2013 | Subramaniyan et al. |
| 2013/0226024 | A1 | 8/2013 | Gopinathan et al. |

(Continued)

FOREIGN PATENT DOCUMENTS

| JP | H04-076256 U | 7/1992 |
| JP | H11-128182 A | 5/1999 |

(Continued)

OTHER PUBLICATIONS

Shimizu; Optical Sensor; Keyence Co Ltd; JP 2014032806 A; Date Published Feb. 20, 2014; (Year: 2014).*

(Continued)

*Primary Examiner* — Nasima Monsur
(74) *Attorney, Agent, or Firm* — MCDONALD HOPKINS LLC

(57) ABSTRACT

A probe apparatus includes a sensor including at least one element, a plurality of electrically conductive wires each of which has a connection portion at which electrical connection is made between the electrically conductive wire and the sensor so that a signal used in the sensor can flow through the electrically conductive wire, and an insulative member configured to cover at least one of the electrically conductive wires at a place nearer to a tip than the connection portion in the at least one electrically conductive wire. The insulative member having an electrical insulating property.

17 Claims, 4 Drawing Sheets

(56) References Cited

U.S. PATENT DOCUMENTS

| | | | |
|---|---|---|---|
| 2014/0032142 A1 | 1/2014 | Dutta et al. | |
| 2014/0142398 A1 | 5/2014 | Patil et al. | |
| 2015/0038833 A1 | 2/2015 | Gopinathan et al. | |
| 2015/0099950 A1 | 4/2015 | Al-Ali et al. | |
| 2016/0128588 A1* | 5/2016 | Melosh | A61B 5/24 607/116 |
| 2016/0202291 A1* | 7/2016 | Gilbert | G01R 15/181 324/750.25 |
| 2017/0332945 A1 | 11/2017 | Gopinathan et al. | |
| 2018/0006388 A1 | 1/2018 | Yamada | |

FOREIGN PATENT DOCUMENTS

| | | |
|---|---|---|
| JP | 2006-288633 A | 10/2006 |
| JP | 2016-165471 A | 9/2016 |
| JP | 2019-080986 A | 5/2019 |
| WO | 2016151762 A1 | 9/2016 |
| WO | 2019097588 A1 | 5/2019 |

OTHER PUBLICATIONS

Miyahara Akihiro et al.; Temperature Sensor And Method Of Manufacturing The Same; NGK Spark Plug Co; Date Published Oct. 17, 2013; DE 102013206836 A1; (Year: 2013).*
Koaizawa Hisashi et al.; Contact Probe, Contact Probe Unit And Electrical Characteristic Measuring Method; Date Published Dec. 18, 2014; JP 2014238330 A; (Year: 2014).*
Office Action for counterpart JP Application 2021-108594 dated Jan. 21, 2025.

* cited by examiner

PROBE APPARATUS AND MANUFACTURING METHOD FOR PROBE APPARATUS

CROSS-REFERENCE TO RELATED APPLICATIONS

The present application claims priority from Japanese Patent Application No. 2021-108594, filed on Jun. 30, 2021, the entire content of which is incorporated herein by reference.

TECHNICAL FIELD

The presently disclosed subject matter relates to a probe apparatus provided with a sensor including at least one element. The presently disclosed subject matter also relates to a method for manufacturing the probe apparatus.

BACKGROUND ART

JP-A-2019-080986 discloses a probe apparatus for acquiring physiological information. The probe apparatus is provided with a sensor that includes a light emitting element and a light detecting element. Light emitted from the light emitting element is detected by the light detecting element after interacting with a living body. Based on intensity of the detected light, physiological information about the living body is acquired. The probe apparatus is provided with a plurality of electrically conductive pads electrically connected to the sensor, and a plurality of electrically conductive wires through any of which a signal used in the sensor can flow. Each of the plurality of electrically conductive wires is connected to a corresponding one of the plurality of electrically conductive pads.

SUMMARY

An object of the presently disclosed subject matter is to enhance resistance to external force applied from an environment while meeting a demand for miniaturization of a probe apparatus.

According to a first aspect for achieving the foregoing object, there is provided a probe apparatus including:
a sensor including at least one element;
a plurality of electrically conductive wires each of which has a connection portion at which electrical connection is made between the electrically conductive wire and the sensor so that a signal used in the sensor can flow through the electrically conductive wire; and
an insulative member configured to cover at least one of the electrically conductive wires at a place nearer to a tip than the connection portion in the at least one electrically conductive wire, the insulative member having an electrical insulating property.

In order to meet a demand for miniaturization of the probe apparatus, a diameter of each of the electrically conductive wires tends to be smaller and a distance between adjacent ones of the electrically conductive wires tends to be narrower. In such a situation, external force applied to the probe apparatus from an environment may cause the adjacent electrically conductive wires to unexpectedly approach each other. According to the aforementioned configuration, contact between the electrically conductive wires is blocked by the insulative member. Accordingly, it is possible to enhance resistance to the external force applied from the environment while meeting the demand for miniaturization of the probe apparatus.

According to a second aspect for achieving the foregoing object, there is provided a probe apparatus including:
a sensor including at least one element; and
a plurality of electrically conductive wires each of which has a connection portion at which electrical connection is made between the electrically conductive wire and the sensor so that a signal used in the sensor can flow through the electrically conductive wire,
wherein adjacent ones of the electrically conductive wires are disposed so that a distance between places nearer to tips than the connection portions in the adjacent electrically conductive wires is wider than a distance between places farther from the tips than the connection portions in the adjacent electrically conductive wires.

In order to meet the demand for miniaturization of the probe apparatus, a cable in which a distance between adjacent ones of electrically conductive wires is narrower tends to be used. According to the aforementioned configuration in which the distance between the adjacent electrically conductive wires is widened toward the tips of the electrically conductive wires, contact between the electrically conductive wires caused by external force applied from an environment may be suppressed even when such a cable is used. Therefore, it is possible to enhance resistance to the external force applied from the environment while meeting the demand for miniaturization of the probe apparatus.

According to a third aspect for achieving the foregoing object, there is provided a method for manufacturing a probe apparatus, the method including the steps of:
preparing a plurality of electrically conductive wires that have been respectively covered with coating members each having an electrical insulating property;
removing a second portion from at least one of the coating members while leaving a first portion therein so as to form an exposed portion where a corresponding one of the electrically conductive wires is exposed, the first portion being at a place nearer to a tip of the corresponding electrically conductive wire, the second portion being at a place farther from the tip; and
electrically connecting the exposed portion to a sensor including at least one element.

When the probe apparatus according to each of the aforementioned aspects is manufactured using the electrically conductive wires covered with the coating members, the step of removing a part from the coating member so as to form the exposed portion where the corresponding electrically conductive wire is exposed for electrical connection is necessary. Since another part left in the coating member through this step is used as an insulative member, the material to be wasted can be reduced. In addition, a step of preparing the insulative member as a separate member and attaching the insulative member to the electrically conductive wire can be dispensed with. Therefore, not only can an increase in material cost be suppressed, but also efficiency in manufacturing work of the probe apparatus can be enhanced.

DESCRIPTION OF EMBODIMENT

With reference to the accompanying drawings, an embodiment will be described in detail below by way of example.

Figure 1:
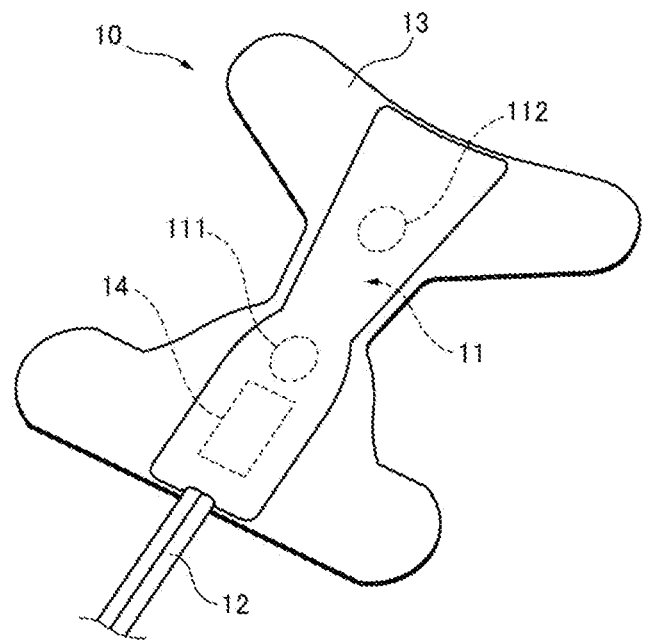
FIG. 1 is a diagram illustrating external appearance of a probe apparatus according to an embodiment.

FIG. 1 illustrates external appearance of a probe apparatus 10 in an embodiment. The probe apparatus 10 is provided with an optical sensor 11, a cable 12, and a support body 13. The optical sensor 11 and the cable 12 are electrically connected to each other. The optical sensor 11 is provided with a light emitter 111 and a light detector 112. The support body 13 supports the light emitter 111 and the light detector 112.

Figure 2:
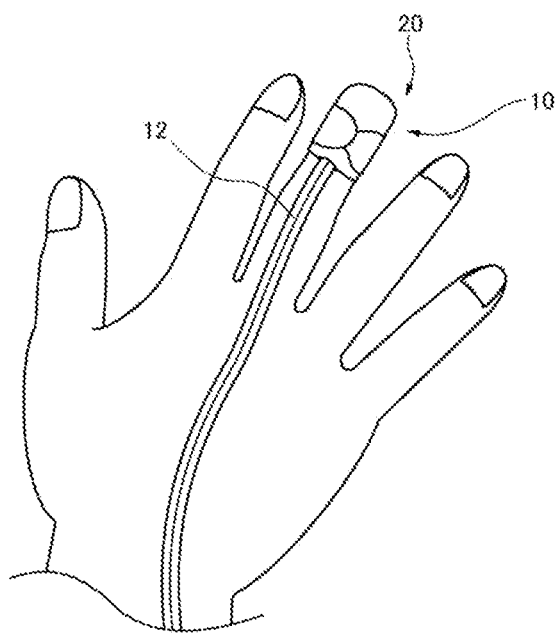
FIG. 2 is a diagram illustrating a state in which the probe apparatus in FIG. 1 has been attached to a fingertip of a subject.

As illustrated in FIG. 2, the probe apparatus 10 is configured to be attached to a fingertip 20 of a subject in order to acquire physiological information of the subject through the optical sensor 11. The fingertip 20 is an example of a living body. Specifically, the support body 13 is wrapped around the fingertip 20 so that the light emitter 111 and the light detector 112 are disposed at positions facing each other across the fingertip 20. The other end of the cable 12 is connected to a physiological information acquisition apparatus (not shown). In the present example, the physiological information acquisition apparatus acquires percutaneous oxygen saturation (SpO2) and a pulse rate as the physiological information.

Figure 3:
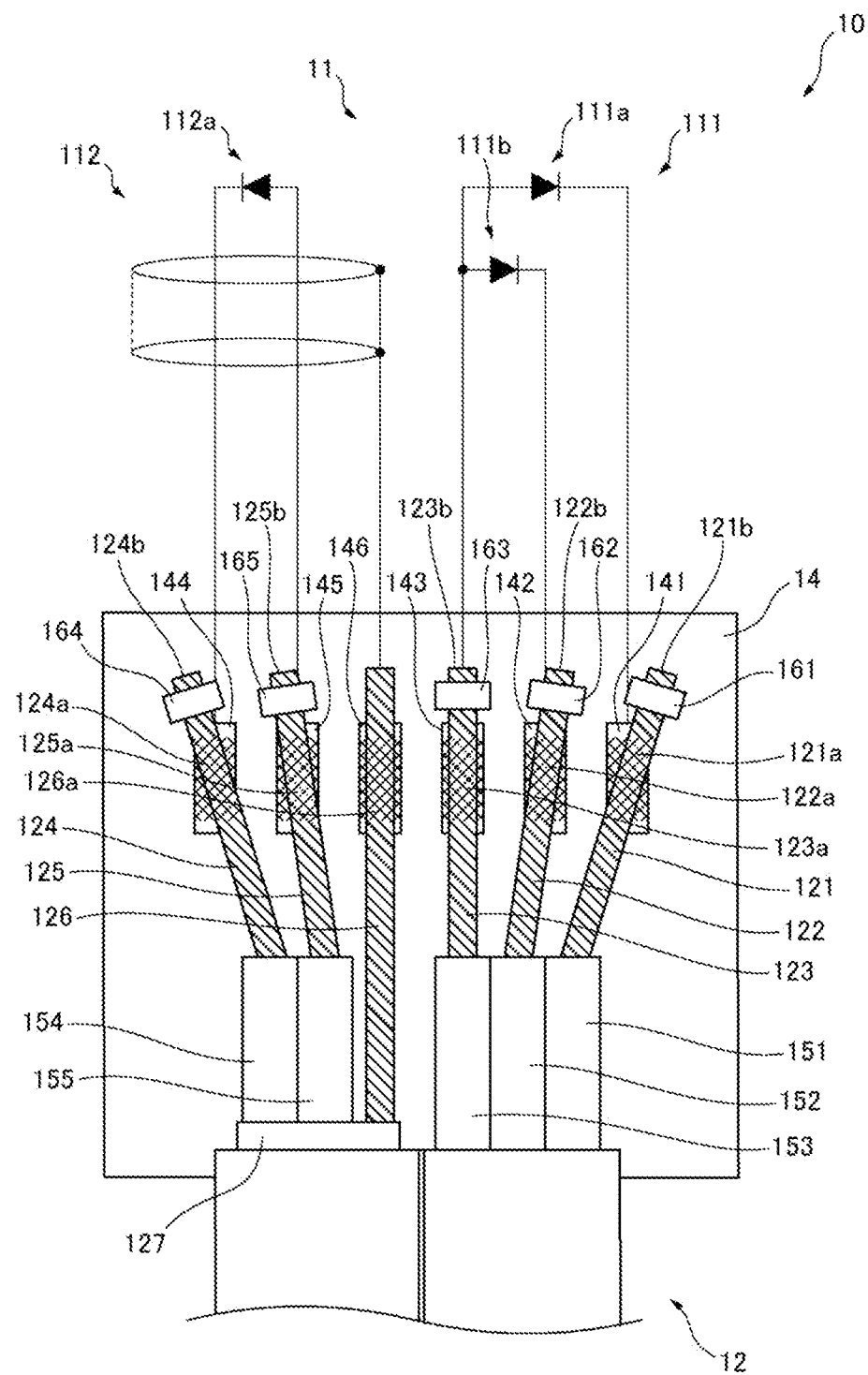
FIG. 3 is a diagram illustrating electrical connection between an optical sensor and a cable in the probe apparatus in FIG. 1.

As illustrated in FIG. 3, the light emitter 111 includes a first light emitting element 111a and a second light emitting element 111b. The first light emitting element 111a is a semiconductor light emitting element that emits red light. The second light emitting element 111b is a semiconductor light emitting element that emits infrared light. Examples of each of the semiconductor light emitting elements include a light emitting diode (LED), a laser diode (LD), an EL element, etc.

The light detector 112 includes a light detecting element 112a. The light detecting element 112a outputs a light detection signal corresponding to an amount of light detected at a light-detecting surface. Examples of the light detecting element include a photodiode, a phototransistor, a photoresistor, etc.

As illustrated in FIG. 1 and FIG. 3, the probe apparatus 10 is provided with a circuit board 14. A circuit which is interposed for electrical connection between the optical sensor 11 and the cable 12 is formed in the circuit board 14. The circuit includes a first contact point 141, a second contact point 142, a third contact point 143, a fourth contact point 144, a fifth contact point 145, and a sixth contact point 146. Each of the first contact point 141, the second contact point 142, the third contact point 143, the fourth contact point 144, the fifth contact point 145, and the sixth contact point 146 is formed of a material having electrical conductivity.

The first contact point 141 is electrically connected to the first light emitting element 111a. The second contact point 142 is electrically connected to the second light emitting element 111b. The third contact point 143 is electrically connected to both the first light emitting element 111a and the second light emitting element 111b. The fourth contact point 144 and the fifth contact point 145 are electrically connected to the light detecting element 112a.

The cable 12 is provided with a first electrically conductive wire 121, a second electrically conductive wire 122, a third electrically conductive wire 123, a fourth electrically conductive wire 124, a fifth electrically conductive wire 125, and a sixth electrically conductive wire 126. Each of the first electrically conductive wire 121, the second electrically conductive wire 122, the third electrically conductive wire 123, the fourth electrically conductive wire 124, the fifth electrically conductive wire 125, and the sixth electrically conductive wire 1 is formed of a material having electrical conductivity.

The first electrically conductive wire 121 has a first connection portion 121a. The first connection portion 121a is a portion at which electrical connection is made between the first electrically conductive wire 121 and the first light emitting element 111a. When the first connection portion 121a is soldered to the first contact point 141, the electrical connection is made between the first electrically conductive wire 121 and the first light emitting element 111a.

The first electrically conductive wire 121 has a portion that is covered with a first coating member 151. The first coating member 151 is formed of a material having an electrical insulating property.

The second electrically conductive wire 122 has a second connection portion 122a. The second connection portion 122a is a portion at which electrical connection is made between the second electrically conductive wire 122 and the second light emitting element 111b. When the second connection portion 122a is soldered to the second contact point 142, the electrical connection is made between the second electrically conductive wire 122 and the second light emitting element 111b is made.

The second electrically conductive wire 122 has a portion that is coated with a second coating member 152. The second coating member 152 is formed of the material having the electrical insulating property.

The third electrically conductive wire 123 has a third connection portion 123a. The third connection portion 123a is a portion at which electrical connection is made between the third electrically conductive wire 123 and the first light emitting element 111a and the second light emitting element 111b. When the third connection portion 123a is soldered to the third contact point 143, the electrical connection is made between the third electrically conductive wire 123 and the first light emitting element 111a and the second light emitting element 111b.

The third electrically conductive wire 123 has a portion that is coated with a third coating member 153. The third coating member 153 is formed of the material having the electrical insulating property.

The fourth electrically conductive wire 124 has a fourth connection portion 124a. The fourth connection portion 124a is a portion at which electrical connection is made between the fourth electrically conductive wire 124 and the light detecting element 112a. When the fourth connection portion 124a is soldered to the fourth contact point 144, the electrical connection is made between the fourth electrically conductive wire 124 and the light detecting element 112a.

The fourth electrically conductive wire 124 has a portion that is coated with a fourth coating member 154. The fourth coating member 154 is formed of the material having the electrical insulating property.

The fifth electrically conductive wire 125 has a fifth connection portion 125a. The fifth connection portion 125a is a portion at which electrical connection is made between the fifth electrically conductive wire 125 and the light detecting element 112a. When the fifth connection portion 125a is soldered to the fifth contact point 145, the electrical connection is made between the fifth electrically conductive wire 125 and the light detecting element 112a.

The fifth electrically conductive wire 125 has a portion that is coated with a fifth coating member 155. The fifth coating member 155 is formed of the material having the electrical insulating property.

With the aforementioned configuration, a signal used in the optical sensor 11 can flow through each of the first electrically conductive wire 121, the second electrically conductive wire 122, the third electrically conductive wire 123, the fourth electrically conductive wire 124, and the fifth electrically conductive wire 125.

Specifically, the first light emitting element 111a emits red light based on a signal flowing from the first electrically conductive wire 121 to the third electrically conductive wire 123. In a similar manner or the same manner, the second light emitting element 111b emits infrared light based on a signal flowing from the second electrically conductive wire 122 to the third electrically conductive wire 123. The emission of the red light by the first light emitting element 111a and the emission of the infrared light by the second light emitting element 111b are performed alternately.

Each of the red light and the infrared light reaches the light-detecting surface of the light detecting element 112a after interacting with tissue of the fingertip 20 of the subject. Signals corresponding to intensity of the red light and intensity of the infrared light at the light-detecting surface flow through the fourth and fifth electrically conductive wires 124 and 125.

Based on a ratio of intensity of the red light incident on the light-detecting surface of the light detecting element 112a to intensity of the red light emitted from the first light emitting element 111a, and a ratio of intensity of the infrared light incident on the light-detecting surface of the light detecting element 112a to intensity of the infrared light emitted from the second light emitting element 111b, percutaneous oxygen saturation of the subject may be calculated. In addition, a pulse rate of the subject may be calculated based on a change of at least one of the two ratios over time.

The cable 12 is provided with a shield layer 127. The shield layer 127 is formed of a material having electrical conductivity. Each of the fourth coating member 154 and the fifth coating member 155 has a portion coated with the shield layer 127. The shield layer 127 is electrically connected to the sixth electrically conductive wire 126.

The sixth electrically conductive wire 126 has a sixth connection portion 126a. The sixth connection portion 126a is a portion at which electrical connection is made between the sixth electrically conductive wire 126 and a protection circuit protecting the fourth electrically conductive wire 124 and the fifth electrically conductive wire 125 from electrostatic noise. When the sixth connection portion 126a is soldered to the sixth contact point 146, the electrical connection is made between the protection circuit and the sixth electrically conductive wire 126.

The probe apparatus 10 is provided with a first insulative member 161. The first insulative member 161 is formed of a material having an electrical insulating property. The first insulative member 161 covers the first electrically conductive wire 121 at a place nearer to a tip 121b of the first electrically conductive wire 121 than the first connection portion 121a.

Thus, even if the first electrically conductive wire 121 unexpectedly approaches the second electrically conductive wire 122 adjacent thereto during or after connection work between the first contact point 141 and the first connection portion 121a, contact between the first electrically conductive wire 121 and the second conductive wire 122 may be blocked due to the first insulative member 161 that plays a role of a spacer.

The probe apparatus 10 is provided with a second insulative member 162. The second insulative member 162 is formed of the material having the electrical insulating property. The second insulative member 162 covers the second electrically conductive wire 122 at a place nearer to a tip 122b of the second electrically conductive wire 122 than the second connection portion 122a.

Thus, even if the second electrically conductive wire 122 unexpectedly approaches the first electrically conductive wire 121 or the third electrically conductive wire 123 adjacent thereto during or after connection work between the second contact point 142 and the second connection portion 122a, contact between the second electrically conductive wire 122 and the first electrically conductive wire 121 or third electrically conductive wire 123 may be blocked due to the second insulative member 162 that plays a role of a spacer.

The probe apparatus 10 is provided with a third insulative member 163. The third insulative member 163 is formed of the material having the electrical insulating property. The third insulative member 163 covers the third electrically conductive wire 123 at a place nearer to a tip 123b of the third electrically conductive wire 123 than the third connection portion 123a.

Thus, even if the third electrically conductive wire 123 unexpectedly approaches the second electrically conductive wire 122 adjacent thereto during or after connection work between the third contact point 143 and the third connection portion 123a, contact between the third electrically conductive wire 123 and the second electrically conductive wire 122 may be blocked due to the third insulative member 163 that plays a role of a spacer.

The probe apparatus 10 is provided with a fourth insulative member 164. The fourth insulative member 164 is formed of the material having the electrical insulating property. The fourth insulative member 164 covers the fourth electrically conductive wire 124 at a place nearer to a tip 124b of the fourth electrically conductive wire 124 than the fourth connection portion 124a.

Thus, even if the fourth electrically conductive wire 124 unexpectedly approaches the fifth electrically conductive wire 125 adjacent thereto during or after connection work between the fourth contact point 144 and the fourth connection portion 124a, contact between the fourth electrically conductive wire 124 and the fifth electrically conductive wire 125 may be blocked due to the fourth insulative member 164 that plays a role of a spacer.

The probe apparatus 10 is provided with a fifth insulative member 165. The fifth insulative member 165 is formed of the material having the electrically insulating property. The fifth insulative member 165 covers the fifth electrically conductive wire 125 at a place nearer to a tip 125b of the fifth electrically conductive wire 125 than the fifth connection portion 125a.

Thus, even if the fifth electrically conductive wire 125 unexpectedly approaches the fourth electrically conductive wire 124 or the sixth electrically conductive wire 126 adjacent thereto during or after connection work between the fifth contact point 145 and the fifth connection portion 125a, contact between the fifth electrically conductive wire 125 and the fourth electrically conductive wire 124 or the sixth electrically conductive wire 126 may be blocked due to the fifth insulative member 165 that plays a role of a spacer.

In order to meet a demand for miniaturization of the probe apparatus, a diameter of each of the electrically conductive wires tends to be smaller and a distance between adjacent ones of the electrically conductive wires tends to be narrower. In such a situation, external force applied to the probe apparatus from the environment may cause the adjacent electrically conductive wires to unexpectedly approach each other. According to the aforementioned configuration, contact between the electrically conductive wires is blocked by the insulative member. Accordingly, it is possible to enhance resistance to the external force applied from the environment while meeting the demand for miniaturization of the probe apparatus.

The first insulative member 161 may be fitted onto the first electrically conductive wire 121 from the tip 121b side prior to the connection work between the first contact point 141 and the first connection portion 121a. However, it is preferable that the first insulative member 161 is a part of the first coating member 151.

Figure 4:
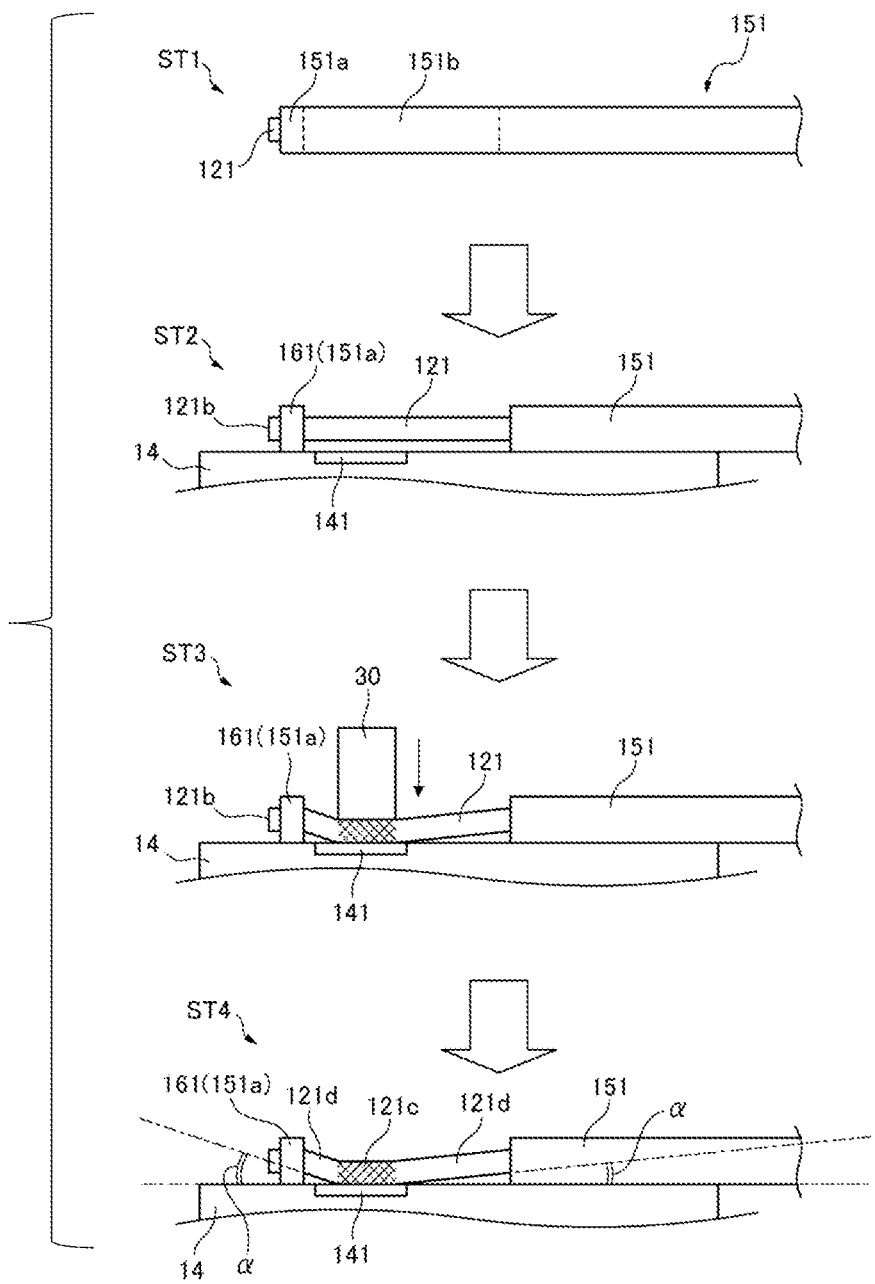
FIG. 4 is a diagram illustrating a method for making the electrical connection between the optical sensor and the cable in the probe apparatus in FIG. 3.

In this case, a part is removed from the first coating member 151 so that the first insulative member 161 is formed, as illustrated in steps ST1 to ST2 in FIG. 4. In other words, the first insulative member 161 is another part of the first coating member 151. Specifically, a second portion 151b that is at a place farther from the tip 121b of the first electrically conductive wire 121 is removed from the first coating member 151 while a first portion 151a that is at a place nearer to the tip 121b of the first electrically conductive wire 121 is left in the first coating member 151. As a result, an exposed portion where the first electrically conductive wire 121 is exposed is formed.

In the case of the configuration where the first electrically conductive wire 121 is covered with the first coating member 151, a step of removing a part from the first coating material 151 to expose the first connection portion 121a for connection work with the first contact point 141 is necessary. Since another part left in the first coating material 151 through this step is used as the first insulative material 161, the material to be wasted can be reduced. In addition, a step of preparing the first insulative member 161 as a separate member and fitting the first insulative member 161 onto the first electrically conductive wire 121 can be dispensed with. Accordingly, not only can an increase in material cost be suppressed but also efficiency in manufacturing work of the probe apparatus 10 can be enhanced.

In the present embodiment, the first electrically conductive wire 121 is a strand wire in which a plurality of electrically conductive thin wires are twisted together. In a case of a configuration in which the first insulative member 161 is fitted as a separate member, it is necessary to perform work while taking care not to disentangle the strand wire. On the other hand, in a case where a part of the first coating material 151 in which the strand wire is bundled from the beginning is used as the first insulative member 161, no special measures are taken but the strand wire can be prevented from being disentangled.

In a similar manner or the same manner, the second insulative member 162 may be fitted onto the second electrically conductive wire 122 from the tip 122b side before the connection work between the second contact point 142 and the second connection portion 122a. However, it is preferable that the second insulative member 162 is a part of the second coating member 152.

In a similar manner or the same manner, the third insulative member 163 may be fitted onto the third electrically conductive wire 123 from the tip 123b side before the connection work between the third contact point 143 and the third connection portion 123a. However, it is preferable that the third insulative member 163 is a part of the third coating member 153.

In a similar manner or the same manner, the fourth insulative member 164 may be fitted onto the fourth electrically conductive wire 124 from the tip 124b side before the connection work between the fourth contact point 144 and the fourth connection portion 124a. However, it is preferable that the fourth insulative member 164 is a part of the fourth coating member 154.

In a similar manner or the same manner, the fifth insulative member 165 can be fitted onto the fifth electrically conductive wire 125 from the tip 125b side before the connection work between the fifth contact point 145 and the fifth connection portion 125a. However, it is preferable that the fifth insulative member 165 is a part of the fifth coating member 155.

As illustrated in a step ST3 in FIG. 4, the exposed portion of the first electrically conductive wire 121 is soldered to the first contact point 141 by an automatic soldering machine 30.

As a result, as illustrated in a step ST4, the first electrically conductive wire 121 has a flat portion 121c and inclined portions 121d when viewed from a direction crossing the plurality of electrically conductive wires included in the cable 12. The flat portion 121c extends along the circuit board 14. Each of the inclined portions 121d extends to be inclined at an angle $\alpha$ with respect to the flat portion 121c.

A distance between the first insulative member 161 and the first coating member 151, an outer diameter of the first insulative member 161, an outer diameter of the first coating member 151, etc. are determined in advance so that the aforementioned angle $\alpha$ is less than 60°. It is preferable that the angle $\alpha$ is less than 30°, and more preferable that the angle $\alpha$ is less than 15°.

According to such a configuration, stress acting to strip the soldered first connection portion 121a of the first electrically conductive wire 121 from the first contact point 141 can be suppressed. Therefore, it is possible to prevent the first connection portion 121a from being unexpectedly stripped from the first contact point 141 by external force etc. applied from the environment.

The aforementioned description about the flat portion and the inclined portions can be also applied to each of the second electrically conductive wire 122, third electrically conductive wire 123, fourth electrically conductive wire 124, and fifth electrically conductive wire 125.

The first insulative member 161 may be formed of a material having thermal contractility. When the first insulative member 161 is a part of the first coating member 151, the first coating member 151 is formed of the material having the thermal contractility.

When the first electrically conductive wire 121 is soldered to the first contact point 141 according to such a configuration, at least the first insulative member 161 is thermally contracted in at least one of radial and axial directions of the first electrically conductive wire 121. Therefore, an increase in the angle $\alpha$ of each of the inclined portions 121d with respect to the flat portion 121c can be suppressed.

In particular, when the first electrically conductive wire 121 is a strand wire, occurrence of a phenomenon that the first electrically conductive wire 121 is disentangled by heat and stress applied due to the soldering may be suppressed by the thermal contraction of the first insulative member 161.

Figure 5:
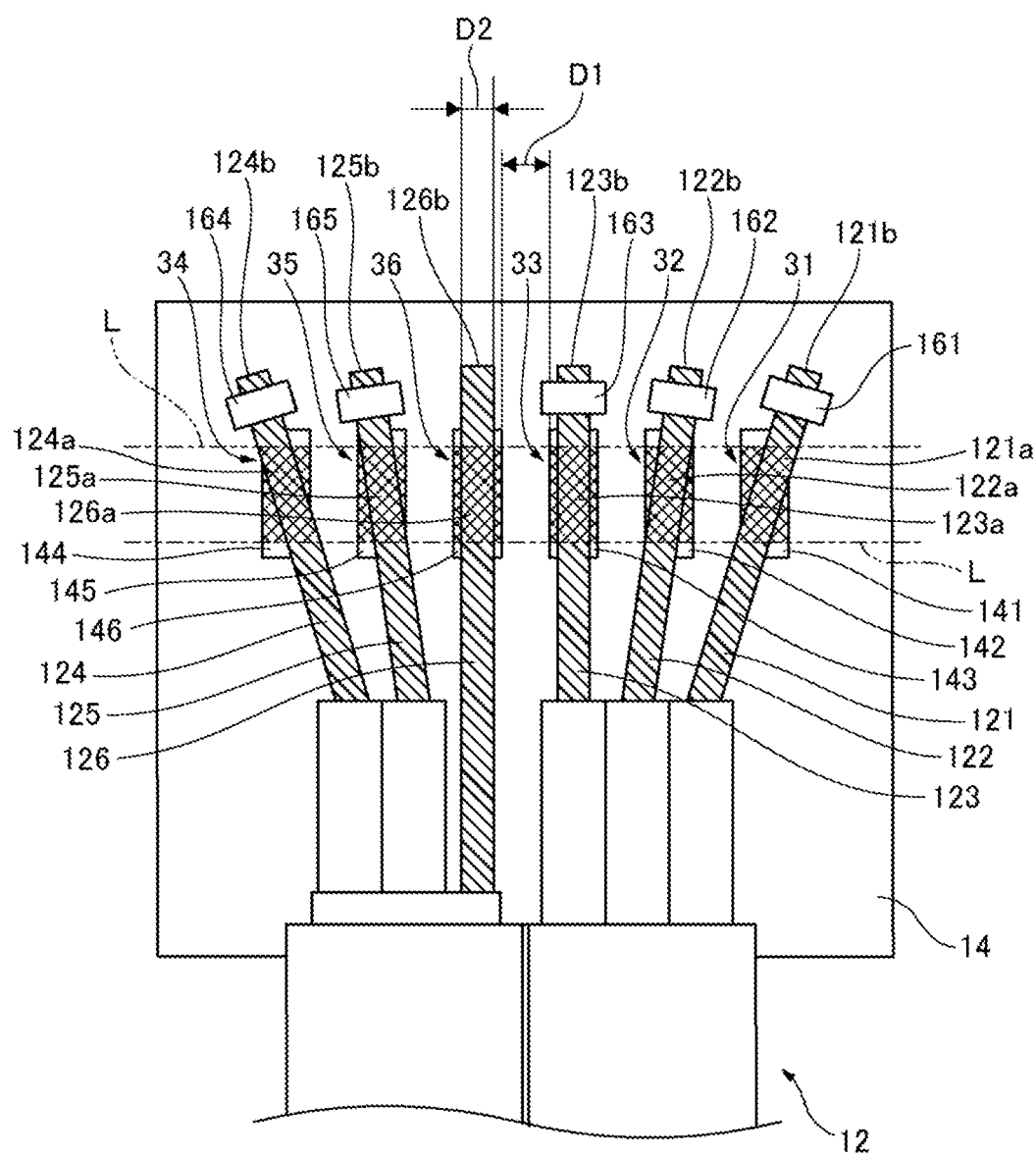
FIG. 5 is a diagram illustrating a detailed configuration of a portion where the electrical connection in FIG. 3 is made.

As illustrated in FIG. 5, the first electrically conductive wire 121 and the second electrically conductive wire 122 adjacent to each other are disposed so that a distance between places nearer to the tip 121*b* and the tip 122*b* than the first connection portion 121*a* and the second connection portion 122*a* in the first electrically conductive wire 121 and the second electrically conductive wire 122 is wider than a distance between places farther from the tip 121*b* and the tip 122*b* than the first connection portion 121*a* and the second connection portion 122*a* in the first electrically conductive wire 121 and the second electrically conductive wire 122.

In a similar manner or the same manner, the second electrically conductive wire 122 and the third electrically conductive wire 123 adjacent to each other are disposed so that a distance between places nearer to the tip 122*b* and the tip 123*b* than the second connection portion 122*a* and the third connection portion 123*a* in the second electrically conductive wire 122 and the third electrically conductive wire 123 is wider than a distance between places farther from the tip 122*b* and the tip 123*b* than the second connection portion 122*a* and the third connection portion 123*a* in the second electrically conductive wire 122 and the third electrically conductive wire 123.

In a similar manner or the same manner, the fourth electrically conductive wire 124 and the fifth electrically conductive wire 125 adjacent to each other are disposed so that a distance between places nearer to the tip 124*b* and the tip 125*b* than the fourth connection portion 124*a* and the fifth connection portion 125*a* in the fourth electrically conductive wire 124 and the fifth electrically conductive wire 125 is wider than a distance between places farther from the tip 124*b* and the tip 125*b* than the fourth connection portion 124*a* and the fifth connection portion 125*a* in the fourth electrically conductive wire 124 and the fifth electrically conductive wire 125.

In a similar manner or the same manner, the fifth electrically conductive wire 125 and the sixth electrically conductive wire 126 adjacent to each other are disposed so that a distance between places nearer to the tip 125*b* and the tip 126*b* than the fifth connection portion 125*a* and the sixth connection portion 126*a* in the fifth electrically conductive wire 125 and the sixth electrically conductive wire 126 is wider than a distance between places farther from the tip 125*b* and the tip 126*b* than the fifth connection portion 125*a* and the sixth connection portion 126*a* in the fifth electrically conductive wire 125 and the sixth electrically conductive wire 126.

The aforementioned configuration can be obtained by a suitable jig with which the tip of at least one of the two adjacent conductive wires is displaced to a plastic deformation region in a direction crossing the axial direction of each of the electrically conductive wires.

In order to meet a demand for miniaturization of the probe apparatus, the cable in which the distance between the adjacent electrically conductive wires is narrower tends to be used. According to the aforementioned configuration where the distance between the adjacent electrically conductive wires is wider toward the tip of each of the electrically conductive wires, contact between the electrically conductive wires caused by external force applied from the environment may be suppressed even when such a cable is used.

When the distance between the tip sides of the adjacent electrically conductive wires is widened appropriately so as to suppress contact between the adjacent electrically conductive wires, an insulative member that plays a role of a spacer may be dispensed with.

In the present embodiment, the first contact point 141, the second contact point 142, the third contact point 143, the fourth contact point 144, the fifth contact point 145, and the sixth contact point 146 are arranged at equal distances in the direction crossing the plurality of electrically conductive wires included in the cable 12. A distance D1 between two adjacent contact points is determined to be larger than a diameter D2 of each of the electrically conductive wires. In the present example, the diameter D2 is 0.3 mm, and the distance D1 is 0.7 mm. Therefore, the distance in the same direction between the connection portions of the two adjacent electrically conductive wires is also larger than the diameter D2 of each of the electrically conductive wires.

In order to meet the demand for miniaturization of the probe apparatus, the electrically conductive wires smaller in diameter tend to be used. Since the dimensions are determined in the aforementioned manner, contact between adjacent ones of the electrically conductive wires due to external force applied from the environment may be suppressed even when such electrically conductive wires are used.

The first contact point 141, the second contact point 142, the third contact point 143, the fourth contact point 144, the fifth contact point 145, and the sixth contact point 146 do not always have to be arranged at the equal distances. As long as the distance between adjacent two of the electrically conductive wires in the direction crossing the plurality of electrically conductive wires is larger than the diameter D2 of each of the electrically conductive wires, the distance in the same direction between any adjacent two of the contact points may be determined appropriately.

Since the automatic soldering machine 30 described with reference to FIG. 4 is used, a first solder mark 31 remains on the first electrically conductive wire 121 and the first contact point 141, as illustrated in FIG. 5. In other words, the first solder mark 31 defines a range of the first connection portion 121*a*. Each of opposite end portions of the first connection portion 121*a* in a direction in which the first electrically conductive wire 121 extends has a shape following a straight line L extending in the direction crossing the plurality of electrically conductive wires included in the cable 12.

In a similar manner or the same manner, a second solder mark 32 remains on the second electrically conductive wire 122 and the second contact point 142. In other words, the second solder mark 32 defines a range of the second connection portion 122*a*. Each of opposite end portions of the second connection portion 122*a* in a direction in which the second electrically conductive wire 122 extends has a shape following the straight line L extending in the direction crossing the plurality of electrically conductive wires included in the cable 12.

In a similar manner or the same manner, a third solder mark 33 remains on the third electrically conductive wire 123 and the third contact point 143. In other words, the third solder mark 33 defines a range of the third connection portion 123*a*. Each of opposite end portions of the third connection portion 123*a* in a direction in which the third electrically conductive wire 123 extends has a shape following the straight line L extending in the direction crossing the plurality of electrically conductive wires included in the cable 12.

In a similar manner or the same manner, a fourth solder mark 34 remains on the fourth electrically conductive wire 124 and the fourth contact point 144. In other words, the fourth solder mark 34 defines a range of the fourth connection portion 124*a*. Each of opposite end portions of the fourth connection portion 124*a* in a direction in which the fourth electrically conductive wire 124 extends has a shape following the straight line L extending in the direction crossing the plurality of electrically conductive wires included in the cable 12.

In a similar manner or the same manner, a fifth solder mark 35 remains on the fifth electrically conductive wire 125 and the fifth contact point 145. In other words, the fifth solder mark 35 defines a range of the fifth connection portion 125*a*. Each of opposite end portions of the fifth connection portion 125*a* in a direction in which the fifth electrically conductive wire 125 extends has a shape following the straight line L extending in the direction crossing the plurality of electrically conductive wires included in the cable 12.

In a similar manner or the same manner, a sixth solder mark 36 remains on the sixth electrically conductive wire 126 and the sixth contact point 146. In other words, the sixth solder mark 36 defines a range of the sixth connection portion 126*a*. Each of opposite end portions of the sixth connection portion 126*a* in a direction in which the sixth electrically conductive wire 126 extends has a shape following the straight line L extending in the direction crossing the plurality of electrically conductive wires included in the cable 12.

The straight line L is an example of a geometric shape. The fact that the shape of the solder mark follows such a geometric shape indicates that the fact that the soldering is performed not manually but by use of the automatic soldering machine 30. The geometric shape may take another form than the straight line in accordance with the shape of the automatic soldering machine 30 that is pressed against the electrically conductive wires. Examples of such a form include two straight lines forming a bent point, a curved line with a single inflection point, etc.

In the example shown in FIG. 5, the end portion near to the tip 121*b* and the end portion far from the tip 121*b* in the first connection portion 121*a* are configured to follow the same geometric shape. However, a geometric shape along which the end portion near to the tip 121*b* extends and a geometric shape along which the end portion far from the tip 121*b* extends may be different from each other. A similar rule or the same rule applies to the second connection portion 122*a*, the third connection portion 123*a*, the fourth connection portion 124*a*, the fifth connection portion 125*a*, and the sixth connection portion 126*a*.

The aforementioned embodiment is merely exemplified in order to facilitate understanding of the presently disclosed subject matter. The configuration of the aforementioned embodiment may be appropriately changed and improved without departing from the spirit of the presently disclosed subject matter.

In the aforementioned embodiment, the optical sensor 11 is provided with the first light emitting element 111*a* that emits red light and the second light emitting element 111*b* that emits infrared light. However, if it is possible to acquire percutaneous oxygen saturation (SpO2), a wavelength of the light emitted from the first light emitting element 111*a* and a wavelength of the light emitted from the second light emitting element 111*b* may be determined appropriately. Specifically, a plurality of wavelengths at which absorbances by oxyhemoglobin in arterial blood corresponding to the SpO2 are substantially different from one another can be selected.

The blood light absorber pertaining to concentration information acquired by use of the optical sensor 11 is not limited to the oxyhemoglobin. Other examples of the blood light absorber include deoxyhemoglobin, carboxyhemoglobin, methemoglobin, a coloring matter, etc. The number of the light emitting elements and the wavelengths may be selected appropriately according to the acquired concentration of the blood light absorber.

In the aforementioned embodiment, the circuit board 14 is built in the support body 13 that supports the optical sensor 11. However, a configuration in which the cable 12 is connected to a connector configured to be removably attached to the support body 13, and the circuit board 14 is installed in the connector may be also used.

The electrically conductive wires included in the cable 12 may be electrically connected to the optical sensor 11 by another method than the soldering to the contact points on the circuit board 14. For example, a method such as deposition, welding, adhesion, or screwing may be used.

The sensor included in the probe apparatus 10 is not limited to the optical sensor 11. The probe apparatus 10 may be provided with any of various sensors detecting information using signals flowing through the electrically conductive wires included in the cable 12. The number of elements included in the sensor may be determined appropriately according to the detected information. The number of the electrically conductive wires may be determined appropriately according to the purpose of the sensor. All of the electrically conductive wires may have portions covered with the coating members, or all of the electrically conductive wires may be not covered with the coating members.

The probe apparatus 10 does not always have to be attached to the fingertip 20 of the subject. The probe apparatus 10 may be attached to an appropriate body part of the subject according to the physiological information acquired by the sensor.

The probe apparatus 10 does not always have to be attached to a living body according to the information acquired by the sensor.

What is claimed is:

1. A probe apparatus comprising:
   a sensor including at least one element;
   a plurality of electrically conductive wires each of which has a first end, a second end, and a connection portion at which electrical connection is made between the electrically conductive wire and the sensor so that a signal used in the sensor can flow through the electrically conductive wire, the connection portion being closer to the first end than to the second end;
   an insulative member that covers at least one of the electrically conductive wires in a region between the first end and the connection portion nearer to a tip of the first end than the connection portion, the insulative member having an electrical insulating property; and
   a coating member that covers a portion of the at least one of the electrically conductive wires,
   wherein the insulative member separately coats each of the at least one electrically conductive wires,
   wherein at the connection portions of each of the electrically conductive wires, the electrically conductive wire is not covered by the insulative member,
   wherein the connection portion of the at least one of the electrically conductive wires is an exposed region between the insulative member and the coating member in a longitudinal direction of the electrically conductive wires,
   wherein the sensor includes a light detecting element,
   wherein the connection portion of the at least one of the electrically conductive wires is a portion at which electrical connection is made between the at least one of the electrically conductive wires and the light detecting element, and wherein the connection portion of the at least one of the electrically conductive wires is soldered to a contact point to make the electrical connection, the contact point being at a substrate on which the connection portion is disposed.

2. The probe apparatus according to claim 1, wherein:
the coating member has an electrical insulating property; and
the insulative member is a part of the coating member.

3. The probe apparatus according to claim 1, wherein the at least one electrically conductive wire is a strand wire in which a plurality of electrically conductive thin wires are twisted together.

4. The probe apparatus according to claim 1, wherein when viewed from a direction along a straight line crossing the electrically conductive wires, each of the electrically conductive wires has a flat portion that extends along the substrate on which the connection portion is disposed, and an inclined portion that extends to be inclined at an angle less than 60° with respect to the flat portion.

5. The probe apparatus according to claim 1, wherein the insulative member is formed of a material that has thermal contractility.

6. The probe apparatus according to claim 1, wherein adjacent ones of the electrically conductive wires are disposed so that a distance between places on the respective adjacent electrically conductive wires nearer to the tips of the first ends than the connection portions in the adjacent electrically conductive wires is wider than a distance between places on the respective adjacent electrically conductive wires farther from the tips of the first ends than the connection portions in the adjacent electrically conductive wires.

7. The probe apparatus according to claim 1, wherein a distance between adjacent ones of the connection portions of the electrically conductive wires is larger than a diameter of each of the electrically conductive wires.

8. The probe apparatus according to claim 7, wherein the diameter is not larger than 0.3 mm and the distance is not larger than 0.7 mm.

9. The probe apparatus according to claim 1, wherein each of opposite end portions of the connection portion in a direction in which each of the electrically conductive wires extends has a shape following a geometric shape crossing the plurality of electrically conductive wires.

10. The probe apparatus according to claim 9, wherein the geometric shape is a single straight line or a curved line with one inflection point.

11. The probe apparatus according to claim 1, wherein the sensor further includes a light emitting element.

12. The probe apparatus according to claim 1, wherein the probe apparatus is removably attached to a living body.

13. A probe apparatus comprising:
a sensor including at least one element; and
a plurality of electrically conductive wires each of which has a first end, a second end, and a connection portion at which electrical connection is made between the electrically conductive wire and the sensor so that a signal used in the sensor can flow through the electrically conductive wire, the connection portion being closer to the first end than to the second end,
wherein adjacent ones of the electrically conductive wires are disposed so that a distance between places on respective adjacent wires nearer to tips of the first ends than the connection portions in the adjacent electrically conductive wires is wider than a distance between places on respective adjacent wires farther from the tips of the first ends than the connection portions in the adjacent electrically conductive wires, and wherein an insulative member separately coats a portion of at least one of the electrically conductive wires in a region between the first end and the connection portion nearer to a tip of the first end than the connection portion, wherein a coating member covers a portion of the at least one of the electrically conductive wires, wherein at the connection portions of the electrically conductive wires, the electrically conductive wire is not covered by the insulative member, wherein the connection portion of the at least one of the electrically conductive wires is an exposed region between the insulative member and the coating member in a longitudinal direction of the electrically conductive wires, wherein the sensor includes a light detecting element, wherein the connection portion of the at least one of the electrically conductive wires is a portion at which electrical connection is made between the at least one of the electrically conductive wires and the light detecting element, and wherein the connection portion of the at least one of the electrically conductive wires is soldered to a contact point to make the electrical connection, the contact point being at a substrate on which the connection portion is disposed.

14. A method for manufacturing a probe apparatus, comprising the steps of:
preparing a plurality of electrically conductive wires that have been respectively covered with coating members having electrical insulation;
removing a second portion from the coating members while leaving a first portion and a third portion therein so as to form an exposed region between the first portion and the third portion where a corresponding one of the electrically conductive wires is exposed and so that the first portion of the coating member separately coats each of the electrically conductive wires, the first portion being at a place nearer to a tip of a first end of the corresponding electrically conductive wire, the second portion being at a place farther from the tip of the first end, and the exposed region being closer to the first end than a second end of the corresponding electrically conductive wire; and
electrically connecting the exposed region to a sensor including at least one element,
wherein the exposed region is between the first portion and the third portion in a longitudinal direction of the electrically conductive wires,
wherein the sensor includes a light detecting element,
wherein the exposed region is a portion at which electrical connection is made between the electrically conductive wires and the light detecting element, and
wherein the exposed region is soldered to a contact point to make the electrical connection, the contact point being at a substrate on which the connection portion is disposed.

15. The method for manufacturing a probe apparatus according to claim 14, wherein:
the coating members are formed of a material that has thermal contractility; and the exposed region is electrically connected to the sensor by soldering.

16. A probe apparatus comprising:
a sensor including at least one element;
a plurality of electrically conductive wires each of which has a first end, a second end, and a connection portion at which electrical connection is made between the electrically conductive wire and the sensor so that a signal used in the sensor can flow through the electrically conductive wire, the connection portion being closer to the first end than to the second end;
an insulative member that covers at least one of the electrically conductive wires in a region between the first end and the connection portion nearer to a tip of the first end than the connection portion, the insulative member having an electrical insulating property; and
a coating member that covers a portion of the at least one of the electrically conductive wires,
wherein at the connection portions of the plurality of electrically conductive wires, the electrically conductive wire is not covered by the insulative member,
wherein each of the electrically conductive wires has, in order from a side of the first end, a portion covered by the insulative member, the connection portion, and a portion covered by the coating member, such that the connection portion of the at least one of the plurality of electrically conductive wires is an exposed region between the insulative member and the coating member in a longitudinal direction of the electrically conductive wires,
wherein the sensor includes a light detecting element,
wherein the connection portion of the at least one of the electrically conductive wires is a portion at which electrical connection is made between the at least one of the electrically conductive wires and the light detecting element, and
wherein the connection portion of the at least one of the electrically conductive wires is soldered to a contact point to make the electrical connection, the contact point being at a substrate on which the connection portion is disposed.

17. A probe apparatus comprising:
a sensor including at least one element; and
a plurality of electrically conductive wires each of which has a first end, a second end, and a connection portion at which electrical connection is made between the electrically conductive wire and the sensor so that a signal used in the sensor can flow through the electrically conductive wire, the connection portion being closer to the first end than to the second end,
wherein adjacent ones of the electrically conductive wires are disposed so that a distance between places on respective adjacent wires nearer to tips of the first ends than the connection portions in the adjacent electrically conductive wires is wider than a distance between places on respective adjacent wires farther from the tips of the first ends than the connection portions in the adjacent electrically conductive wires,
wherein each of the electrically conductive wires has, in order from a side of the first end, a portion covered by an insulative member, the connection portion, and a portion covered by a coating member, such that at the connection portions of the plurality of electrically conductive wires, the electrically conductive wire is not covered by the insulative member, and such that the connection portion of the at least one of the plurality of electrically conductive wires is an exposed region between the insulative member and the coating member in a longitudinal direction of the electrically conductive wires,
wherein the sensor includes a light detecting element,
wherein the connection portion of the at least one of the electrically conductive wires is a portion at which electrical connection is made between the at least one of the electrically conductive wires and the light detecting element, and
wherein the connection portion of the at least one of the electrically conductive wires is soldered to a contact point to make the electrical connection, the contact point being at a substrate on which the connection portion is disposed.

* * * * *